United States Patent [19]

Quiachon et al.

[11] Patent Number: 5,256,150
[45] Date of Patent: Oct. 26, 1993

[54] LARGE-DIAMETER EXPANDABLE SHEATH AND METHOD

[75] Inventors: Dinah B. Quiachon, San Jose; Wesley D. Sterman, San Francisco; Ronald G. Williams, Menlo Park; David C. Dillow, Cupertino; Steven G. Baker, Sunnyvale, all of Calif.

[73] Assignee: EndoVascular Technologies, Inc., Menlo Park, Calif.

[21] Appl. No.: 807,089

[22] Filed: Dec. 13, 1991

[51] Int. Cl.⁵ ............................................. A61M 5/00
[52] U.S. Cl. ............................ 604/171; 604/164; 604/167; 604/169
[58] Field of Search .............. 604/164, 165, 166, 167, 604/169, 170, 171, 256, 280, 282

[56] References Cited

U.S. PATENT DOCUMENTS

| | | | |
|---|---|---|---|
| 2,844,351 | 7/1958 | Smith | 604/250 |
| 4,311,136 | 1/1982 | Weikl et al. | 604/164 |
| 4,401,433 | 8/1983 | Luther | 604/159 |
| 4,540,411 | 9/1985 | Bodicky | 604/169 |
| 4,580,573 | 4/1986 | Quinn | 604/169 |
| 4,601,713 | 7/1986 | Fuqua | 604/280 |
| 4,738,666 | 4/1988 | Fuqua | 604/280 |
| 4,857,062 | 8/1989 | Russell | 604/167 |
| 5,015,239 | 5/1991 | Browne | 604/280 |
| 5,066,285 | 11/1991 | Hillstead | 604/164 |

FOREIGN PATENT DOCUMENTS

150281  8/1985  European Pat. Off. ............ 604/166

Primary Examiner—Gene Mancene
Assistant Examiner—Frank A. LaViola
Attorney, Agent, or Firm—Fulwider, Patton, Lee & Utecht

[57] ABSTRACT

A large-diameter expandable sheath for use in introducing a catheter into a vessel in the body of a patient comprising an elongate sheath tube formed of a flexible material which has proximal and distal extremities and a passage extending therethrough of a maximum predetermined diameter. The distal extremity of the elongate sheath tube is folded longitudinally to a smaller folded diameter. A backflow adapter is secured to the proximal extremity of the elongate sheath tube. The backflow adapter has a central opening therein in registration with the passage in the sheath tube. A valve is disposed in the central opening of the backflow adapter and is movable between open and closed positions. The valve when open permits the catheter to be inserted into the sheath, and when closed serves to form a hemostatic seal about the catheter.

13 Claims, 5 Drawing Sheets

LARGE-DIAMETER EXPANDABLE SHEATH AND METHOD

BACKGROUND OF THE INVENTION

This invention relates to an expandable sheath and more particularly to a large-diameter expandable sheath and method.

Expandable access catheter assemblies have heretofore been provided to facilitate the placement and removal of diagnostic and therapeutic catheters through the vascular system. Such catheter assemblies included a flexible variable-diameter catheter body, a diameter control stylet and a flexible Y-hub. The flexible Y-hub incorporates an adjustable hemostasis valve and a side port in one branch and a diameter control stylet guide wire in another branch. A flexible variable diameter catheter body is secured to the flexible Y-hub and can be expanded between a collapsed position and an expanded position by the stylet guide wire. Several deficiencies have been found in such a device. For example, the adjustable hemostasis valve is incapable of accepting large catheters. The flexible variable-diameter catheter body is objectionable in that it has a tendency to reduce in diameter and hold onto large-diameter catheters when it is attempted to place the same through the catheter body. In addition, the tip of the stylet guide wire catches a large-diameter catheter which causes elongation of the catheter body and reduction in its diameter to grab and prevent further advancement of the large-diameter catheter. There is therefore a need for a new and improved large-diameter expandable sheath which will overcome these deficiencies.

SUMMARY OF THE INVENTION

In general, it is an object of the present invention to provide an expandable sheath which can be utilized with large-diameter catheters and method for using the same.

Another object of the invention is to provide a sheath of the above character which is folded longitudinally to a small diameter and which can be expanded greatly when a large-diameter catheter is to be passed through it.

Another object of the invention is to provide a sheath of the above character which is provided with a backflow adapter which includes a tubular diaphragm that can be moved into an hourglass or iris-like configuration to create a fluid-tight barrier around any tubular device such as a large-diameter catheter passed through the backflow adapter and the tubular diaphragm.

Another object of the invention is to provide a sheath of the above character in which a dilator can be utilized for expanding the sheath.

Another object of the invention is to provide a sheath of the above character in which the backflow adaptor can be readily controlled.

Additional objects and features of the invention will appear from the following description in which the preferred embodiments are set forth in detail in conjunction with the accompanying drawings.

DESCRIPTION OF THE PREFERRED EMBODIMENTS

In general, the large-diameter expandable sheath is used for introduction of a catheter into the body of a patient. It comprises an elongate sheath tube formed of a flexible material and having proximal and distal extremities and having passage therein of a predetermined maximum diameter. The distal extremity of the elongate sheath tube is folded longitudinally into a smaller diameter. A backflow adapter is secured to the proximal extremity of the elongate sheath tube. The backflow adapter has a central opening therein in registration with the passage in the sheath tube. Valve means is disposed in the central opening in the backflow adapter and is movable between open and closed positions. The valve means when in an open position permits a catheter to be introduced into the sheath and when closed forms a liquid-tight seal about the catheter extending therethrough.

Figure 1:
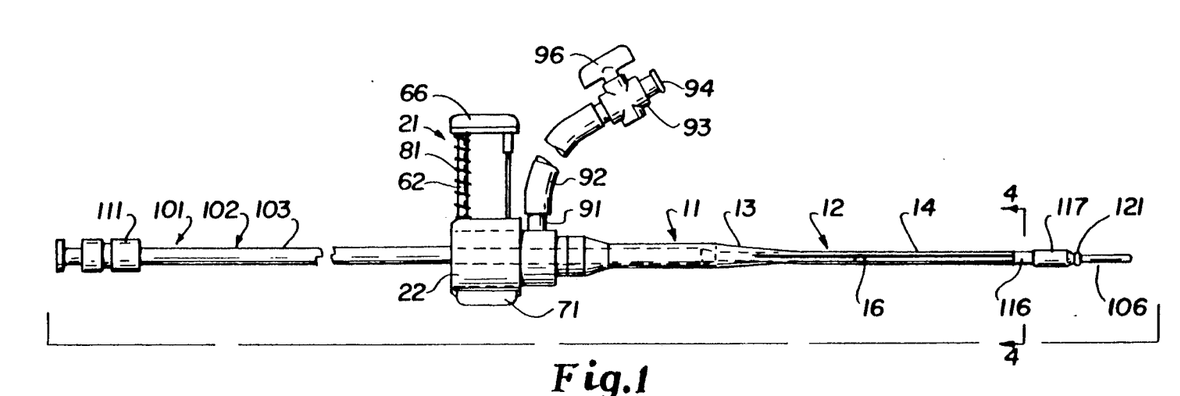
FIG. 1 is a side elevational view of a large-diameter expandable sheath assembly incorporating the present invention and in which a sheath introducer is disposed in the sheath.

More particularly as shown in FIG. 1 of the drawings, the large-diameter expandable sheath 11 consists of an elongate sheath tube 12 having proximal and distal extremities 13 and 14 and having a flow passage 16 having a maximum diameter extending therethrough. The expandable sheath 11 can have a suitable length as, for example, 15–35 centimeters and preferably approximately 18 centimeters with a maximum outside diameter of 1 centimeter. The elongate sheath tube is formed of a flexible material having a wall thickness of 0.001 to 0.020 inches and preferably about 0.005 inches and can be formed of a suitable plastic material such as Teflon TM (a fluorinated ethylene polypropylene). An alternate material is Tefzel TM (ethylene tetrafluoroethylene). The selected material should have physical characteristics which will not be compromised by radiation sterilization.

Figure 4:
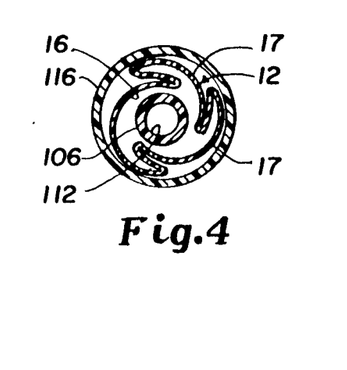
FIG. 4 is a cross-sectional view taken along the line 4—4 of FIG. 1.

The distal extremity of the sheath tube, as shown in FIG. 4, is pleated or folded longitudinally to provide wraps or folds 17 for a distance of approximately 10 centimeters from the distal end to provide a distal extremity of reduced diameter as, for example, a reduction of the outside diameter from $\frac{3}{8}''$ to 3/16″ or approximately one-half the original size. The folding or pleating of the sheath tube 12 in this manner serves two purposes. The first purpose is to reduce the sheath diameter to facilitate introduction of the sheath and to make it less traumatic for the vessel into which it is introduced. The second reason is that with a small-diameter, thin-wall tube, as represented by the elongate sheath tube 12, there is less likelihood of kinking occurring than in a large-diameter, thin-wall tube. The distal extremity of the sheath tube 12, when folded longitudinally in this manner, serves to provide kink resistance in the distal extremity 14 while still being relatively flexible.

Figures 5, 6, 7:
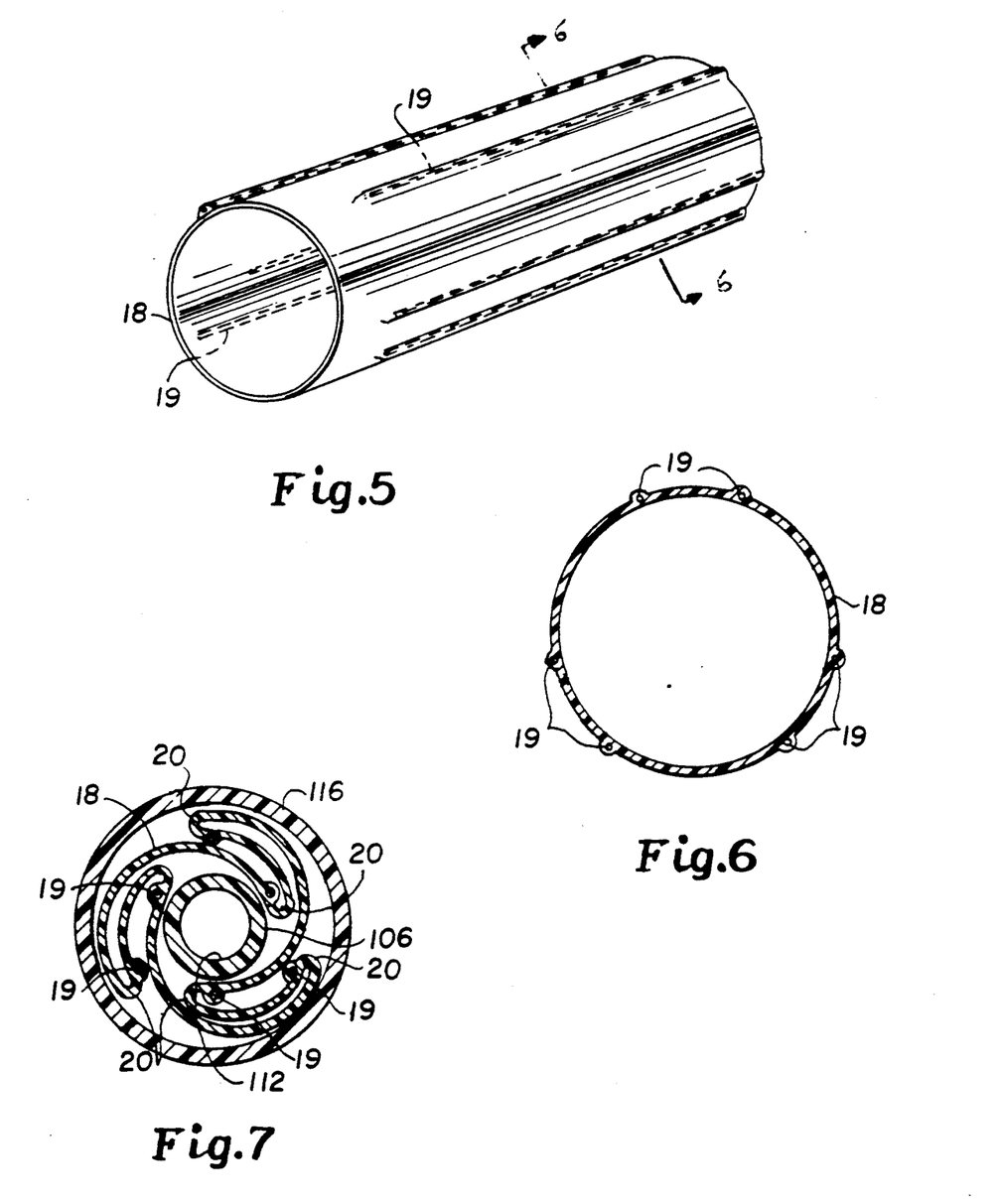
FIG. 5 is a partial side elevational view of an alternative embodiment of an expandable sheath incorporating the present invention.
FIG. 6 is a cross-sectional view taken along the line 6—6 of FIG. 5.
FIG. 7 is a cross-sectional view similar to FIG. 4 showing the sheath of FIGS. 5 and 6.

If it is desired to further decrease the likelihood of kinking in the large-diameter, thin-wall tube which forms the sheath tube 12, another embodiment of the sheath tube can be provided of the type shown in FIGS. 5, 6 and 7. The sheath tube 18 shown in those figures is provided with a plurality of circumferentially spaced apart flexible elongate elements 19 which are embedded in the wall of the tube 18 and extend longitudinally along the length thereof as shown in FIG. 5. The proximal extremities are offset or staggered as shown in FIG. 5 with alternate elements 19 being shorter. This offset relationship provides a gradation in stiffness in the proximal extremity of the sheath tube 18. The elongate elements 19 can be in the form of stainless steel wires having a diameter ranging from 0.005″ to 0.015″ and preferably a diameter of approximately 0.010″. As can be seen from FIG. 6, the sheath tube 18 can bulge outwardly around the elongate elements 19 while being relatively thin between the elongate elements to retain the flexibility of the tube 18. As also can be seen from FIG. 6, the elongate elements 19 are spaced apart in the three groups to facilitate the formation of six folds 20 as shown in FIG. 7. Thus, by way of example, each set of elongate elements can have the elongate elements spaced approximately 35° apart with each set being spaced approximately 85° apart. Spacing of the elongate elements 19 in this manner facilitates the formation of the folds shown in FIG. 7. The elongate elements 19 also provide additional rigidity longitudinally of the tube 18 so as to inhibit accordioning of the tube 18 during removal of the introducer as hereinafter described.

Figure 8:
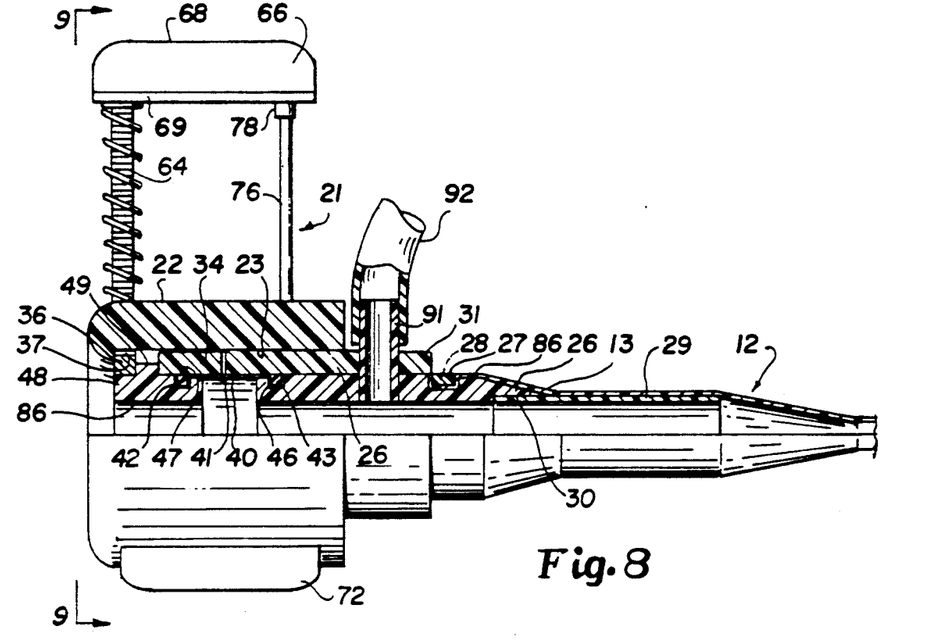
FIG. 8 is an enlarged side elevational view partially in cross-section of the proximal extremity of the large expandable sheath of the sheath assembly shown in FIG. 1 and particularly showing the backflow adapter.

A backflow adapter 21 is secured to the proximal extremity of the elongate sheath tube 12. The backflow adapter 21 consists of a housing or body 22 which is formed of a suitable material, such as plastic. The housing 22 is provided with a central bore 23 extending therethrough in axial alignment with the passage 16 of the sheath tube 12. A cylindrical sheath tube adapter 26 is disposed in the bore 23 and is provided with an annular recess 27 which receives an inwardly-extending flange 28 provided on the proximal extremity 13 of the sheath tube 12 (see FIG. 8). A tubular insert 29 formed of the same material as the sheath tube 12 but of a greater wall thickness, as for example twice the wall thickness of the sheath tube 12, is secured within an annular recess 30 in the sheath tube adapter 26 by suitable means such as an adhesive. The insert 29 serves as a reinforcement and serves to prevent collapse of the proximal extremities 13 of the sheath tube 12 when the expandable sheath 11 is used. The sheath tube adapter 26 is fixed within a first cylindrical collar 31 seated within the bore 23 and is held in place by solvent bonding the cylindrical collar 31 into the housing or body 22 to prevent longitudinal and/or rotational movement of the first collar 31 relative to the housing or body 22. A second collar 34 is also seated in the bore 23 and is rotatable therein. An annular ring gear 36 having teeth 37 thereon is also rotatably mounted in the bore 23 as hereinafter described.

A cylindrical or tubular valve member or diaphragm 40 is disposed between the first and second collars 31 and 34, and is provided with a bore or flow passage 41 extending therethrough. The valve member 40 is provided with inwardly extending annular lips or flanges 42 and 43 provided on opposite extremities of the same (see FIGS. 8 and 14). The flange 43 is seated in an annular recess 46 in the sheath tube adapter 26 and is retained therein by the first collar 31. The flange 42 is seated in an annular recess 47 provided in a retaining ring 48 and retained therein by the second collar 34. An annular protrusion 49 is formed integral with the retaining ring 48 and engages one side of the toothed ring gear 36 which is secured to the retaining ring 48 by suitable means such as an adhesive. Similarly, the retaining ring 48 functionally engages the second collar 34 and causes the second collar 34 to rotate therewith.

Figure 14:
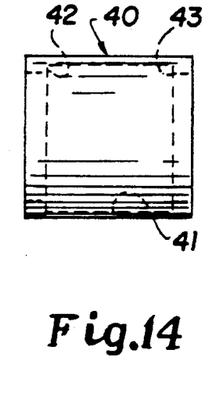
FIG. 14 is a side elevational view of the valve or diaphragm utilized in the backflow adapter shown in FIGS. 9 and 10.

The diaphragm or valve member 40 can have a suitable size as, for example, a length of 0.30–0.45″ inches, and preferably a length of approximately 0.30″ inches, and an inside diameter of 0.35–0.500″, and preferably an inside diameter of 0.375″, with a wall thickness ranging from 0.005″ to 0.015″, and preferably a wall thickness of 0.007″. The annular lips 42 and 43 can extend inwardly for a distance of 0.032″ from the outer wall surface and have a length of approximately 0.050″. The diaphragm or valve member 40 can be formed of a suitable material, such as a silicone elastomer, as, for example, Dow Silastic 97-4720. It can have a Shore A hardness ranging from 20–80 and preferably a Shore hardness of 40A. Alternatively, a low durometer, tear-resistant rubber-like latex material can be utilized.

Figure 15:
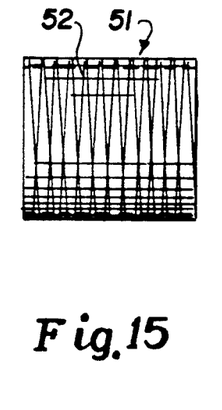
FIG. 15 is an alternative embodiment of a valve or diaphragm for use in the backflow adapter shown in FIGS. 9 and 10.
Figure 16:
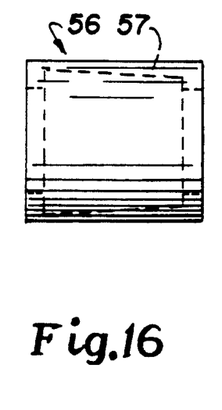
FIG. 16 is still another embodiment of a valve or diaphragm for use in the backflow adapter show in FIGS. 9 and 10.

Other diaphragm or valve members such as shown in FIGS. 15 and 16 can be utilized which have the same physical conformation. In the embodiment shown in FIG. 15, small diener polyester fibers 52 are bonded to the exterior surface of the diaphragm 51 with a silicone adhesive so that the fibers 52 extend circumferentially around the outside surface of the diaphragm 51. Such fibers serve to impede radial and longitudinal distention of the diaphragm or valve member 51. The diaphragm or valve member 56 shown in FIG. 16 is provided with a cylindrical wall 57 which increases in thickness in a direction towards the distal extremity of the diaphragm. This helps the diaphragm to withstand the pressures applied to the diaphragm during use, which may cause the diaphragm to distend and leak.

Figure 11:
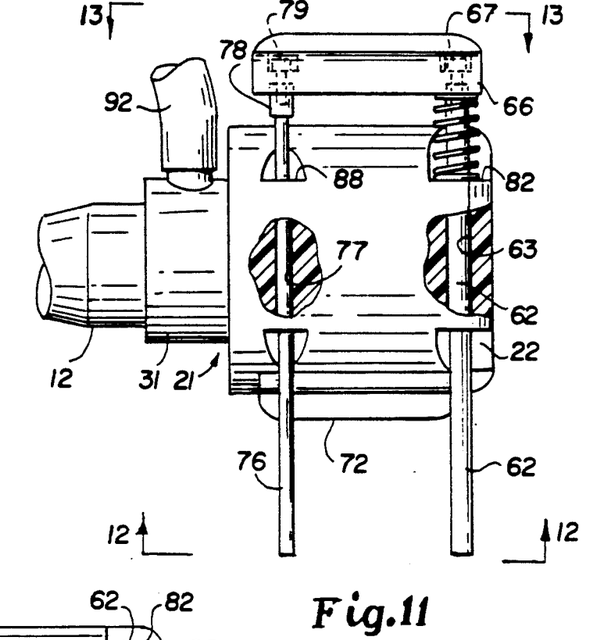
FIG. 11 is a side elevational view partially in cross section opposite the side shown in FIG. 8 of the proximal extremity of the expandable sheath.

Means is provided for causing relative rotation between the sheath tube adapter 26 and the retaining ring 48 for opening and closing the bore or flow passage 41 by twisting of the cylindrical valve member or diaphragm 40. This is accomplished by fixing the first collar 31 and the sheath tube adapter 26 within the housing or body 22 by suitable means such as solvent bonding and causing rotation of the retaining ring 48 by the use of a rack 61. The rack 61 consists of a rod 62 formed of a suitable material such as stainless steel which extends through a hole 63 (see FIG. 11) in the housing or body 22 in a direction which is tangential of the bore 23. The rod 62 is disposed immediately adjacent a flange 64 formed in the body 22 against which the ring gear 36 rotates. The hole 63 opens into the bore 23 so that rack teeth 64 provided on the one side of the rod 62 engage the toothed ring gear 36 whereby upon reciprocatory movement of the rack 61, the ring gear 36 is rotated through an angle ranging from 180° to 360°, and preferably an angle of at least 270°.

Figure 12:
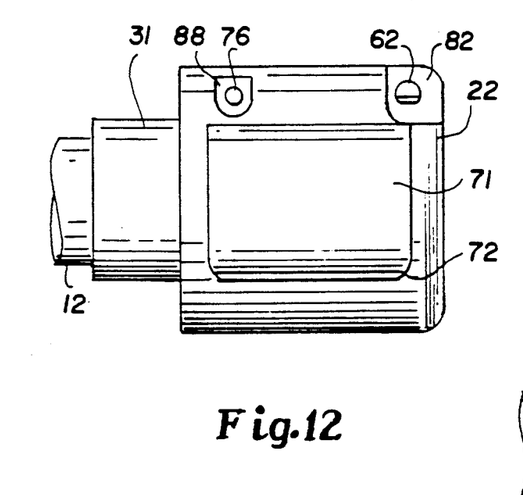
FIG. 12 is a bottom plan view looking along the line 12—12 of FIG. 11.
Figure 13:
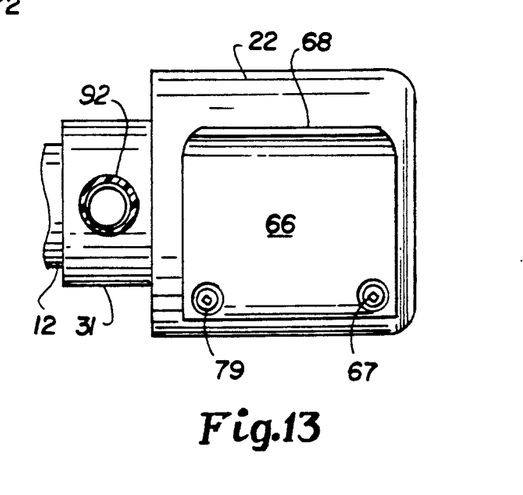
FIG. 13 is a top plan view looking along the line 13—13 of FIG. 11.

An actuator 66 formed of a suitable material such as plastic is mounted on the upper extremity of the rod 62 and is secured thereto by suitable means such as an Allen-head screw 67 set into the rod 62, as shown in FIG. 13. The actuator 66 is generally rectangular in plan and is provided with an upstanding lip 68 so that it conforms to the conformation of the index finger of the hand which is to be utilized for actuating the rack 61. The actuator 66 is provided with a reinforcing rib 69 along one edge of the same. A similar actuator member 71 is provided on the body 22 underlying the actuator 66 and is also provided with a downwardly extending lip 72. The actuator member 71 is secured to the body 22 by suitable means such as an adhesive. The member 71 also has a rectangular configuration in plan and is sized so that it is adapted to be engaged by the thumb of the hand, as shown in FIG. 12. Thus, one hand can be utilized for operating the backflow adapter 21 by the index finger of the hand grasping the actuator 66 and the thumb of the same hand grasping the member 71.

A stabilization and guide rod 76 extends through a tangential bore 77 (see FIG. 11) provided in the body 22 which is spaced apart from the bore 63 and extends in a direction which is parallel thereto. The rod 76 is formed of a material such as stainless steel and is provided with a collar 78 which extends through the reinforcing rib 69 of the actuator 66 and is secured therein by suitable means such as an Allen-head screw 79.

Figure 9:
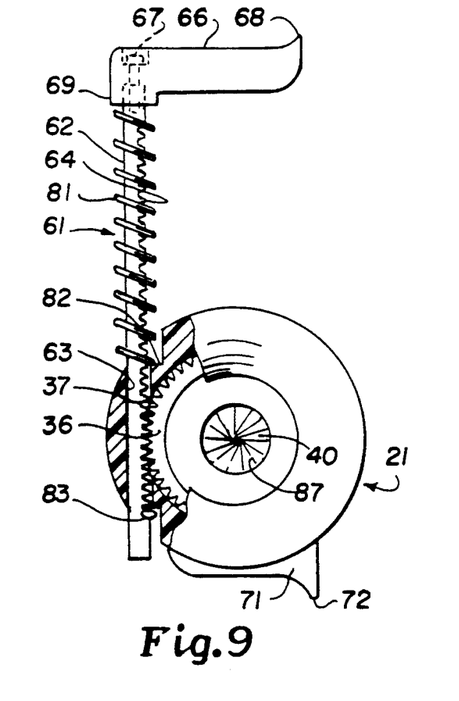
FIG. 9 is an end elevational view looking along the line 9—9 of FIG. 8 with certain portions being shown in cross-section and with the valve carried by the backflow adapter being in a normally closed position.
Figure 10:
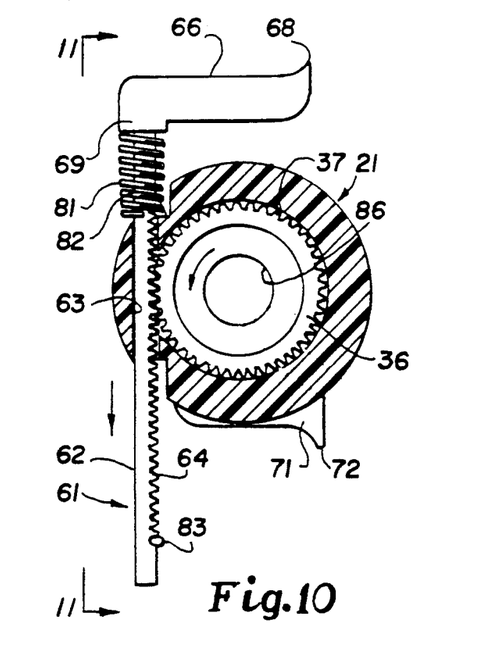
FIG. 10 is a view similar to FIG. 9, but showing the valve in an open position.

Means is provided for yieldably returning the rack 61 into a position so that the valve member or diaphragm 40 is in a normally closed position and consists of a coil spring 81 coaxially mounted on the rod 62 and having one end engaging the actuator 66 and having the other end engaging a seat 82 provided in the body 22. Means is provided for preventing the spring 81 from urging the rod 62 out of the bore 63 and consists of a lump 83 of solder or a braising material provided on the rod 62 adjacent the lower extremity of the rack teeth 64. Thus, it can be seen by the hand engaging the backflow adapter 21 using the index finger to engage the actuator 66 and the thumb to engage the actuator member 71, the rack 61 can be reciprocated back and forth to open and close a bore 86 extending through the retaining ring 48 and the sheath tube adapter 26 by forming an hourglass or iris-like closure as shown in FIG. 9 in which the radially extending lines 87 shown represents the folding over of the elastomeric material of the valve member or diaphragm 40. The collar 78 provided on the stabilization rod 76 serves to stop further travel up the rack when the collar 78 engage a seat 88 provided in the body 22. In this position, the spring 81 is almost completely compressed as shown in FIG. 10. Following the release of the actuator 66, the spring 81 returns the rack 62 to its home position and causes the valve member or diaphragm 40 to be completely closed as shown in FIG. 9.

The ring gear 36 can be formed of a suitable material such as stainless steel and can have any suitable number of teeth. Alternatively, the ring gear can be formed of a suitable plastic such as Nylon TM. The other portions of the backflow adapter 21 as, for example, the body 22, the first collar 31, the second collar 34, the retaining ring 48 can be formed of a suitable plastic such as polycarbonate. The metal parts such as the rod 62, the stabilization rod 76 and the spring 81 can be formed of a suitable material such as stainless steel.

Means is provided for introducing liquid as, for example, a radiopaque liquid, into the bore 86 and consists of a tube 91 formed of a suitable material such as plastic extending through the first collar 31 and through the sheath tube adapter 26 so that it is in communication with the bore 86. Flexible tubing 92 is connected to the tube 91 and has a stopcock 93 of a conventional type mounted thereon which is provided with a Luer-type fitting 94. The stopcock 93 is provided with a knob 96 which can be utilized for moving the stopcock 93 between open and closed positions.

Figure 2:
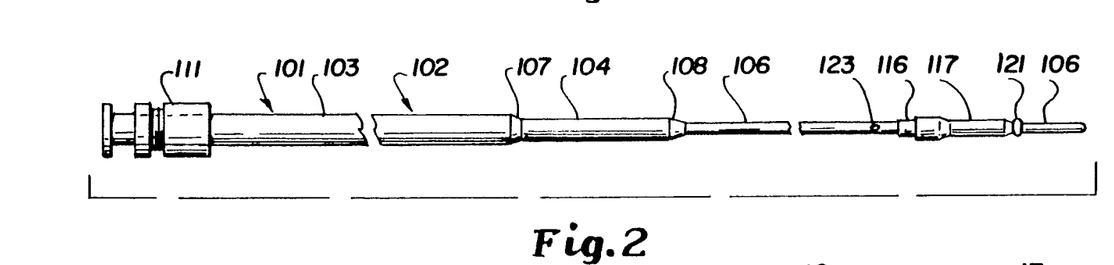
FIG. 2 is an enlarged side elevational view of the sheath introducer shown in the large-diameter expandable sheath assembly of FIG. 1.

A sheath introducer 101 is provided as a part of the assembly shown in FIG. 1 and as shown in FIG. 2 consists of an elongate tubular member 102 formed in three sections 103, 104 and 106 of different diameters. The elongate tubular member 102 can be formed of a suitable plastic material such as Pebax TM which is formed of polyether Block Amides which is loaded with approximately 10% barium sulfate to make the same visible under X-rays. Section 103 can have a diameter ranging from 0.15" to 0.30" and preferably an outside diameter of 3/16ths of an inch. The section 104 can have a suitable diameter as, for example, 0.08" to 0.15" and preferably a diameter of ⅛ of an inch. The section 106 can have a diameter ranging from 0.06" to 0.12" and preferably a diameter of 0.08". The distal extremities of the sections 103 and 104 are provided with tapers 107 and 108, respectively, so as to provide a tapered transition from one diameter to another. A Luer-type fitting 111 is mounted on the proximal extremity of the tubular section 103. A bore or lumen 112 (see FIG. 4) of a suitable size as, for example, one capable of passing a 0.038" guidewire, is provided in the section 106 as well as in the sections 104 and 103 extending the length of the tubular member 102. A tube 116 is mounted on the section 106 and the distal extremity of the same and is formed of a suitable material such as silicone and is retained thereon in a suitable matter by the use of polyethylene shrink tubing 117. A cylindrical enlargement or annular bump 121 is provided on the tubular section 106 adjacent the distal extremity of the shrink tubing 117 and serves to prevent the sleeve 116 and the shrink tubing 117 from accidentally slipping off of the distal extremity of the tubular section 106.

Figure 3:
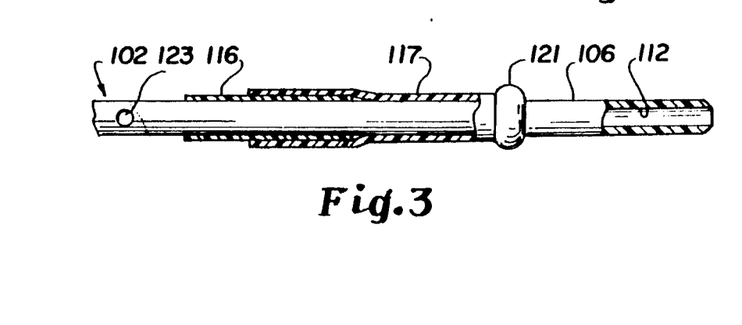
FIG. 3 is an enlarged detail view partially in cross-section of the distal extremity of the sheath introducer shown in FIG. 2.

When the sheath introducer 101 is disposed in the expandable sheath 11, as shown in FIG. 1, the proximal extremity of the silicone sleeve 116 is disposed over the distal extremity of the sheath tube 12 and serves to prevent the sharp edges of the folded sheath tube 12 from causing trauma to the interior wall of a vessel when it is introduced into the vessel when the sheath is introduced as hereinafter described. A vent hole 123 is provided in the sheath introducer 101 which is in communication with the passage 112 proximal of the silicone sleeve 116, as shown in FIG. 3. The vent hole 123 can be utilized for flushing the elongate sheath tube 12 through the side port fitting 94 prior to use of the expandable sheath in a surgical procedure.

Operation and use of the expandable sheath 11 in conjunction with the sheath introducer 101 may now be briefly described as follows. Let it be assumed that the patient has been prepared in a conventional manner and that it is desired to enter a peripheral vessel such as an artery or a vein of the patient. The desired vessel is exposed and a longitudinal or transverse incision made into that vessel. A guidewire of a suitable size is then selected as, for example, a guidewire having a diameter of 0.038". The guidewire (not shown) is introduced into the vessel and then the expandable sheath assembly 11 shown in FIG. 1 is placed over the guidewire by placing the proximal extremity of the guidewire into the lumen 112 provided in the elongate tubular member 102 and advanced through the Luer fitting 111. The rounded tip and the small diameter of the section 106 of the tubular member 102 facilitate advancement of the sheath introducer 101 into the vessel without traumatizing the vessel. The small-diameter tip section 106 is followed by the elongate sheath tube 12 which has been collapsed as hereinbefore described about the tubular section 106 until the sheath tube 12 has been introduced to the proper depth in the vessel. As soon as the sheath tube 12 has been positioned in the vessel, the sheath introducer 101 is advanced relative to the elongate sheath tube 12 by using one hand to hold the backflow adapter 21 which is connected to the sheath tube 12 and the other hand to push the sheath introducer 101 so that the proximal extremity of the silicone sleeve 116 moves off of the distal extremity of the sheath tube 12 to expose the same.

As soon as this has been accomplished, the sheath introducer 101 is pushed forward so that section 103 enters the collapsed section of the sheath tube 12 to commence opening of the same. The sheath introducer 101 is then removed through the backflow adapter 21. The sheath introducer can be removed by grasping the backflow adapter 21 by the fingers of the hand as hereinafter described to at least partially open the same to permit removal of the sheath introducer and dilator 101 while minimizing the flow of blood from the sheath tube 12. The backflow adapter can then be released. The sheath 11 and its backflow adapter is now in its normally closed state to provide a hemostatic seal closing the flow passage 86.

The physician conducting the procedure then selects the desired catheter or other device which is desired to be introduced through the expandable sheath 11. Such a device should have a diameter of 8.5 mm or less or which is at least slightly less than the diameter of the bore 86. The physician grasps the actuator members 66 and 71 and presses the same to operate the rack 61 to open the diaphragm or valve member 40 permitting the physician to insert the device as, for example, the catheter through the expandable sheath 11. As soon as the catheter has been advanced as far as desired, the physician releases the pressure on the actuator members 66 and 71 permitting the diaphragm 40 to close around the device as, for example, the catheter inserted through to form a hemostatic seal about the catheter. If it is desired to reposition the catheter, it is merely necessary to push or pull the catheter and it will slide freely through the diaphragm. When it is desired to remove the catheter, the catheter need only be pulled out of the sheath 101 and the diaphragm will seal closed forming a hemostatic seal.

After the procedure has been completed, the expandable sheath 11 can be removed from the vessel and the incision which has been made in the vessel for permitting passage of the expandable sheath can be sutured.

It can be seen from the foregoing that there has been provided an expandable sheath 11 which can be made in various sizes to accommodate large-diameter devices while still providing the desired hemostatic seal. The expandable sheath can be readily inserted and removed. The sheath introducer 101 facilitates this introduction. It is provided with a distal extremity 106 which is small in diameter to permit the sheath tube 12 to be wrapped about the same as hereinbefore described. The sheath introducer 101 is provided with sections 103 and 104 of larger diameters to provide additional rigidity to the sheath introducer 101 to facilitate pushing of the sheath introducer when introducing the expandable sheath 11 into the vessel of the patient.

Figure 17:
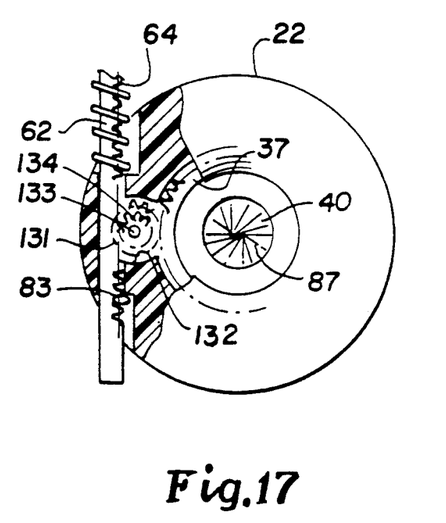
FIG. 17 is a view similar to FIG. 9 but showing an alternative rack and pinion arrangement for the backflow adapter.

An alternative mechanism for actuating the diaphragm 40 is shown in FIG. 17 and consists of a pinion 131 which engages the ring gear 36 and is disposed in a cylindrical recess 132 provided in the body 22. The pinion 131 is mounted on a shaft 133. Another gear 134 is mounted on the shaft 133 and has a smaller diameter than the diameter of the pinion 131 and engages the rack teeth 64 provided on the rod 62. By providing such a gear arrangement, it can be seen that it is possible to provide a shorter rack to achieve the same degree of ring gear rotation for opening and closing of the diaphragm 40.

Figure 18:
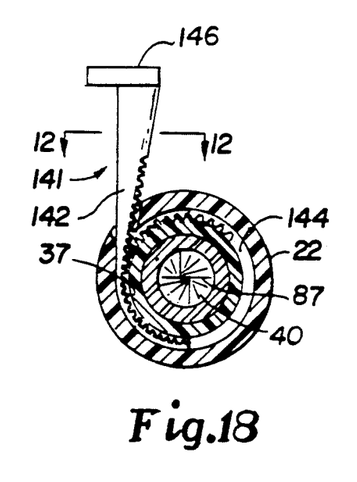
FIG. 18 is a cross-sectional view showing another embodiment of a rack for the closing and opening of the valve in the backflow adapter.
Figure 19:
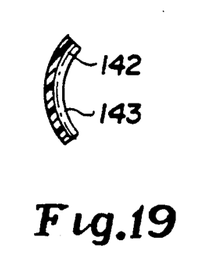
FIG. 19 is a cross-sectional view taken along the line 12—12 of FIG. 18.

As can be seen in FIGS. 18 and 19, there is shown another embodiment of a mechanism for actuating the diaphragm 40. As shown therein it consists of a flexible rack 141 that is comprised of a flexible member 142 which is provided with rack teeth 143 on one side of the same which are adaptable to engage the ring gear 36. The member 142 extends through a semicircular slot 144 provided in the body so that it extends through the body and around the ring gear 36. An actuator 146 is provided formed integral with the rack 141 for operating the rack 141 with the fingers of the hand. In this construction the rack is substantially contained within the body 22.

We claim:

1. In a large-diameter expandable sheath for use in introducing a catheter into a corporeal vessel,
an elongate sheath tube formed of a flexible material having proximal and distal extremities and having a passage extending therethrough of a maximum predetermined diameter;
the distal extremity of said sheath tube being folded longitudinally to a smaller folded diameter;

a backflow adapter secured to the proximal extremity of said sheath tube;

said backflow adapter having a central opening therein in registration with the passage in said sheath tube and having valve means disposed in the central opening of said backflow adapter and movable between open and closed positions;

wherein the valve means when open permits the catheter to be inserted into said sheath tube and when closed forms a hemostatic seal about the catheter;

wherein the valve means is in the form of a cylindrical member formed of a flexible material and having a bore therein in registration with the central opening of said backflow adaptor;

said back flow adaptor having means for engaging the opposite ends of the cylindrical member for causing relative rotation between the ends of the cylindrical member to cause the cylindrical member to be twisted to close the bore extending through the cylindrical member; and said means for causing rotation between the opposite ends of the cylindrical member includes a retaining ring, a sheath tube adapter secured to opposite ends of the cylindrical member, means for fixing the sheath tube adapter to prevent rotation of the same within said back flow adaptor, and means for rotating the retaining ring with respect to the sheath tube adapter.

2. A sheath as in claim 1 wherein said means for causing rotation includes a ring gear secured to said retaining ring and rack means for driving said ring gear to cause rotation of the same.

3. A sheath as in claim 2 together with means yieldably engaging said rack for urging said rack means into a position wherein said cylindrical member is moved to provide valve means which is in a normally closed position.

4. A sheath as in claim 5 wherein said rack means extends tangentially through said body together with actuator means carried by the rack adapted to be engaged by the fingers of the hand for moving the rack against the force of the yieldable means to move the valve means to an open position.

5. A sheath as in claim 4 together with a stabilizer rod slidably mounted within said body parallel to said rack and secured to said actuator means.

6. A sheath as in claim 5 together with means carried by the rack for preventing said yieldable means from pulling said rack means out of engagement with said cylindrical member.

7. In a large-diameter expandable sheath for use in introducing a catheter into a corporeal vessel, an elongate sheath tube formed of a flexible material having proximal and distal extremities and having a passage extending therethrough of a maximum predetermined diameter;

the distal extremity of said sheath tube being folded longitudinally to a smaller folded diameter;

a backflow adapter secured to the proximal extremity of said sheath tube;

said backflow adapter having a central opening therein in registration with the passage in said sheath tube and having valve means disposed in the central opening of said backflow adapter and movable between open and closed positions;

wherein the valve means when open permits the catheter to be inserted into said sheath tube and when closed forms a hemostatic seal about the catheter; and a sheath introducer disposed in the passage of said sheath tube to form an assembly, said sheath introducer having a distal extremity extending beyond the proximal extremity of said sheath tube and dilation means mounted on the distal extremity of said sheath introducer with has a diameter greater than the folded diameter of said sheath tube.

8. In a large-diameter expandable sheath tube assembly for use in a corporeal vessel, an elongate flexible sheath tube having proximal and distal extremities and having a passage extending therethrough of a maximum diameter;

a backflow adapter mounted on the proximal extremity of said sheath tube;

a sheath introducer disposed in said backflow adapter and extending through the passage in said sheath tube;

said sheath introducer comprising an elongate tubular member having a proximal extremity and a distal extremity having a reduced diameter from the proximal extremity;

the distal extremity of said sheath tube being folded over the distal extremity of the elongate tubular member of said sheath introducer to a folded diameter;

said sheath introducer having sleeve means for covering the folded distal extremity of said sheath tube to prevent the folded distal extremity of the sheath tube from causing trauma to the vessel when the sheath tube is introduced into the vessel;

means for securing said sleeve means on the elongate tubular member of said sheath introducer so that said sheath introducer can be pushed distally with respect to said sheath tube to cause said sleeve means to be removed from the distal extremity of said sheath tube to permit said sheath tube to expand and to push the proximal extremity of said sheath introducer through the distal extremity of said sheath tube to expand said sheath tube; and said means for securing said sleeve means on the elongate tubular member of said sheath introducer includes a length of shrink tubing extending over said sleeve means and having a diameter greater than said sleeve means.

9. An assembly as in claim 8 together with means carried by the distal extremity of the sheath introducer to prevent the shrink tubing from being separated from the distal extremity of the sheath introducer.

10. A sheath tube introducer comprising:

a flexible elongate tubular member having proximal and distal extremities:

a fitting positioned at the proximal extremity of said tubular member;

sleeve means positioned at the distal extremity of said tubular member;

said sleeve means having a proximal expandable extremity and a distal extremity;

securing means for preventing the distal extremity of said sleeve means from being separated from the distal extremity of said tubular member; and said securing means includes a length of shrink tubing mounted on said sleeve means.

11. A sheath introducer as in claim 10 wherein the proximal extremity of the flexible elongate tubular member is of greater diameter to provide additional rigidity to the flexible elongate tubular member and to provide a means of dilating the distal extremity of the sheath tube.

12. A sheath tube introducer comprising:
a flexible elongate tubular member having proximal and distal extremities:
a fitting positioned at the proximal extremity of said tubular member;
sleeve means positioned at the distal extremity of said tubular member;
said sleeve means having a proximal expandable extremity and a distal extremity;
securing means for preventing the distal extremity of said sleeve means from being separated from the distal extremity of said tubular member; and
said tubular member having a flow passage therein together with an opening formed in said tubular member proximal of the proximal extremity of said sleeve means and in communication with the flow passage.

13. In a method for introducing an expandable sheath into the vessel in the body of a patient by the use of an expandable sheath having an elongate sheath tube with proximal and distal extremities and having a passage extending therethrough of maximum diameter and having a backflow adapter provided on the proximal extremity, and a sheath introducer having an elongate tubular member with proximal and distal extremities with an expandable sleeve mounted on the distal extremity, introducing the sheath introducer into the backflow adapter and into the sheath tube so that the distal extremity of the sheath introducer extends beyond the distal extremity of the sheath tube, folding the proximal extremity of the sheath tube longitudinally to wrap the same over the distal extremity of the sheath introducer, expanding the sleeve on the sheath introducer over the distal extremity of the folded sheath tube to thereby prevent the sheath tube from causing trauma to the wall of a vessel of the patient with it is introduced into the vessel of the patient, introducing the combination of the expandable sheath and the sheath introducer into the vessel of the patient, advancing the sheath introducer relative to the expandable sheath so that the sleeve is separated from the distal extremity of the sheath tube to permit the sheath tube to expand, further advancing the sheath introducer through the distal extremity of the sheath tube to cause further expansion of the distal extremity of the sheath tube, and removing the sheath introducer from the expandable sheath.

* * * * *

UNITED STATES PATENT AND TRADEMARK OFFICE
CERTIFICATE OF CORRECTION

PATENT NO. : 5,256,150

DATED : October 26, 1993

INVENTOR(S) : Dinah B. Quiachon, Wesley D. Sterman, Ronald G. Williams, David C. Dillow and Steven G. Baker It is certified that error appears in the above-indentified patent and that said Letters Patent is hereby corrected as shown below:

Column 1, line 59, replace "adaptor" with --adapter--.

Column 1, above line 65, insert the heading --Brief Description of the Drawings--.

Column 6, line 51, replace "1/8" with --1/8th--.

Column 6, line 65, replace "matter" with --manner--.

Column 9, line 14, replace "adaptor" with --adapter--.

Column 9, line 15, replace "back flow" with --backflow--.

Column 9, line 26, replace "adaptor" with --adapter--.

Column 9, line 26, replace "back flow" with --backflow--.

Column 9, line 39, replace "claim 5" with --claim 3--.

Column 10, line 8, replace "with" with --which--.

Column 10, line 53, replace "extremities:" with --extremeties;--.

Column 11, line 5, replace "extremities:" with --extremeties;--.

UNITED STATES PATENT AND TRADEMARK OFFICE
CERTIFICATE OF CORRECTION

PATENT NO. : 5,256,150

DATED : October 26, 1993

INVENTOR(S) : Dinah B. Quiachon, Wesley D. Sterman, Ronald G. Williams, David C. Dillow and Steven G. Baker It is certified that error appears in the above-indentified patent and that said Letters Patent is hereby corrected as shown below:

Column 12, line 14, replace "with" with --when--.

Signed and Sealed this

Twenty-seventh Day of May, 1997

Attest:

BRUCE LEHMAN

Attesting Officer

Commissioner of Patents and Trademarks